United States Patent
Rupasree Ragini et al.

(10) Patent No.: US 7,306,857 B2
(45) Date of Patent: Dec. 11, 2007

(54) BINUCLEAR ORGANOMETALLIC COMPLEXES AND ORGANIC ELECTROLUMINESCENCE DEVICE USING THE SAME

(75) Inventors: Das Rupasree Ragini, Suwon-si (KR); Seok Chang, Daejeon-si (KR); Jong-hyoup Lee, Seoul (KR); Lyong-sun Pu, Suwon-si (KR); Eun-sil Han, Daejeon-si (KR); Hae-jung Son, Seoul (KR); Ji-hoon Lee, Daejeon-si (KR)

(73) Assignee: Samsung SDI Co., Ltd., Suwon (KR)

( * ) Notice: Subject to any disclaimer, the term of this patent is extended or adjusted under 35 U.S.C. 154(b) by 495 days.

(21) Appl. No.: 10/932,228

(22) Filed: Sep. 2, 2004

(65) Prior Publication Data

US 2005/0069728 A1 Mar. 31, 2005

(30) Foreign Application Priority Data

Sep. 6, 2003 (KR) ...................... 10-2003-0062371

(51) Int. Cl.
*H01L 51/54* (2006.01)
*C09K 11/06* (2006.01)

(52) U.S. Cl. ...................... 428/690; 428/917; 313/504; 257/40; 257/E51.044; 546/4; 556/13; 556/18; 556/21

(58) Field of Classification Search ...................... None
See application file for complete search history.

(56) References Cited

U.S. PATENT DOCUMENTS

2002/0048689 A1 4/2002 Igarashi et al.

2002/0064681 A1 5/2002 Takiguchi et al.
2004/0026663 A1* 2/2004 Heuer et al. ........... 252/301.16

FOREIGN PATENT DOCUMENTS

| EP | 1 191 613 A2 | 3/2002 |
| WO | 02/15645 A1 | 2/2002 |
| WO | 03/063555 A1 | 7/2003 |

OTHER PUBLICATIONS

Synthesis and Properties of Platinum (II) 2-(2-Pyridyl)thiophenide Complexes and Ruthenium (II) Bisbipyridyl Complexes with 1,2-Bis(diphenylphosphino)ethene; K. P. Balashev et al., Russian Journal of General Chemistry, vol. 71, No. 7, 2001, pp. 1151-1152.
Synthesis of Complexes of Platinum (II) with C,N,N'-terdentate Schiff Base Donor Ligands. Crystal and Molecular Structure of [Pt{3-Me-4-MeOC$_6$H$_2$C(H)=NCH$_2$CH$_2$NMe$_2$}(Me)]; José M. Vila et al.; Journal of Organometallic Chemistry, vol. 566; 1998; pp. 93-101.

* cited by examiner

*Primary Examiner*—Marie Yamnitzky
(74) *Attorney, Agent, or Firm*—H.C. Park & Associates, PLC

(57) ABSTRACT

Provided are binuclear organometallic complexes enabling highly efficient phospholuminescence and an organic electroluminescent device using the same. The binuclear organometallic complexes, which are suitably used for forming an organic layer of the organic electroluminescent device, provides maximum luminescence emission in the wavelength range of 400-650 nm, and induces white electroluminescence when combined with green or red luminescent materials.

13 Claims, 4 Drawing Sheets

BINUCLEAR ORGANOMETALLIC COMPLEXES AND ORGANIC ELECTROLUMINESCENCE DEVICE USING THE SAME

CROSS-REFERENCE TO RELATED APPLICATION

This application claims the priority of Korean Patent Application No. 2003-62371, filed Sep. 6, 2003, in the Korean Intellectual Property Office, the disclosure of which is incorporated herein in its entirety by reference.

BACKGROUND OF THE INVENTION

1. Field of the Invention

The present invention relates to the binuclear organometallic complexes and organic electroluminescence devices using the same, and more particularly, to binuclear organometallic complexes capable of emitting light of wavelengths from the blue range to the red range from the triplet metal-to-ligand charge transfer (MLCT) state and an organic electroluminescence device using the same as the emitting layer forming material.

2. Description of the Related Art

Generally, an organic electroluminescent device (hereinafter referred to as EL) may include an anode, a hole injection layer, a hole transport layer, a light-emitting layer, an electron transport layer, an electron injection layer, and a cathode. These layers may be sequentially formed on a substrate. The hole transport layer, the light-emitting layer, and the electron transport layer may be organic layers made of organic compounds. The organic electroluminescence device having the above-described configuration may be driven as follows.

When a voltage is applied between the anode and the cathode, holes injected from the anode migrate to the light-emitting layer via the hole transport layer. Electrons emitted from the cathode are injected into the light-emitting layer via the electron transport layer. The electrons and the holes recombine in the light-emitting layer to generate excitons. As the excitons transition from an excited state to a base state, energy is transferred to luminescent molecules in the light-emitting layer, enabling the molecules to emit light and display images.

Materials for forming the light-emitting layer of the organic EL device may be classified as fluorescent materials that use a singlet or phosphorescent materials which use a triplet. The fluorescent material or the phosphorescent material or the material in combination with an appropriate host material may form a light-emitting layer. As a result of electron excitation, singlet excitons and triplet excitons are produced in the host. Statistically, the singlet excitons and the triplet excitons in an OLED are created in a ratio of about 1:3.

Conventional organic EL devices that us a fluorescent material as a material for forming a light-emitting layer may be disadvantageous in that triplets from the host may be wasted. However, organic EL devices using a phosphorescent material as a material for forming a light-emitting layer are advantageous in that singlet excitons and triplet excitons are both utilized. Such phosphorescent materials can use all of the 75% triplet excitons for emission and offers higher luminescent efficiency compared to fluorescent materials using only 25% singlet excitons for emission.

Various phosphorescent materials employing metallic complexes of Iridium or platinum as luminescent materials using triplet excitons have been discussed. However, materials satisfying requirements for realizing a full-color display of high emission efficiency or white electroluminescence with low power consumption have been restricted to ones emitting in the green and red ranges. Blue phosphorescent materials, however, have not been reported, making it difficult to achieve a full-color display, which is, in turn, becoming a barrier to the development of phospholuminescent full-color display devices.

To address the above-described problems, intensive development of blue luminescent materials is under way (See, for example, WO 02/15645 and U.S. Patent Pub. No. 2002/0064681). Also, there have been proposed organometallic complexes having a bulky functional group, e.g., a phosphine group, or a functional group having a high ligand field intensity, e.g., a cyano group, introduced thereto to increase a difference between HOMO-LUMO energy levels by transforming the molecular geometry. Specific examples of the organometallic complexes include iridium (III) complexes having cyclometalating phenyl pyridine and a phosphine group. The iridium (III) complexes are mononuclear complexes having the general formula of $Ir(ppy)_2P(X)_3Y$ (X=phenyl, phenoxy or n-butyl, Y=Cl or CN.), as described in US2002/0048689 A1.

SUMMARY OF THE INVENTION

The present invention provides binuclear organometallic complexes capable of efficiently emitting light over a wide wavelength range from the blue region to the red region from the triplet metal-to-ligand charge transfer (MLCT) state. The present invention also provides an organic electroluminescence device using the same.

In an aspect of the present invention, there is provided a binuclear organometallic complex represented by Formula 1:

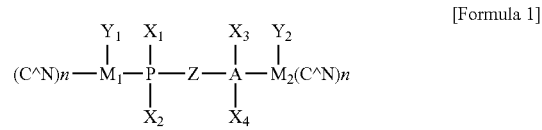

[Formula 1]

wherein (C^N) represents a cyclometalating ligand bonded to M through nitrogen (N) and carbon (C);

$M_1$ and $M_2$ are independently Ru, Rh, Pt, Os or Ir;

$X_1$, $X_2$, $X_3$, and X4 are independently a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, a substituted or unsubstituted $C_4$-$C_{20}$ cycloalkyl, substituted or unsubstituted $C_6$-$C_{20}$ aryl, substituted or unsubstituted $C_2$-$C_{20}$ heteroaryl, substituted or unsubstituted $C_6$-$C_{20}$ aryloxy, substituted or unsubstituted $C_6$-$C_{20}$ heteroaryloxy, substituted or unsubstituted $C_2$-$C_{20}$ alkoxycarbonyl, substituted or unsubstituted $C_1$-$C_{20}$ acyloxy, substituted or unsubstituted $C_2$-$C_{20}$ acylamino, substituted or unsubstituted $C_2$-$C_{20}$ alkoxycarbonylamino, substituted or unsubstituted $C_2$-$C_{20}$ aryloxycarbonylamino, substituted or unsubstituted sulfonylamino, —N(R')(R"), where R' and R" are independently hydrogen, or a $C_1$-$C_{20}$ alkyl group, sulfamoyl, substituted or unsubstituted $C_1$-$C_{20}$ alkylcarbamoyl, carbamoyl, substituted or unsubstituted $C_6$-$C_{20}$ arylcarbamoyl, substituted or unsubstituted $C_6$-$C_{20}$ arylthio, substituted or unsubstituted $C_2$-$C_{20}$ heteroarylthio, sulfonyl, sulfinyl, ureido, phosphonic acid, amido, hydroxy, mercapto, halogen atom, cyano, carboxyl, substituted or unsubstituted $C_2$-$C_{20}$ alkylcarboxyl, nitro, hydroxamic acid, sulfino, hydrazine, imino, substituted or unsubstituted $C_1$-$C_{20}$ silylalkyl, or substituted or unsubstituted $C_1$-$C_{20}$ alkylphosphino group;

$Y_1$ and $Y_2$ are independently a halogen atom, SCN, CNO, CN, RCOO(R=substituted or unsubstituted $C_1$-$C_{20}$ alkyl, substituted or unsubstituted $C_6$-$C_{20}$ aryl, or substituted or unsubstituted $C_2$-$C_{20}$ heteroaryl), pyrazolate, imidazolate, amido, imido groups;

A is phosphorus (P) or nitrogen (N);

Z is a substituted or unsubstituted $C_1$-$C_{20}$ alkylene, substituted or unsubstituted $C_2$-$C_{20}$ alkenylene, substituted or unsubstituted $C_6$-$C_{20}$ arylene, —$(CH_2)_2P(C_6H_5)(CH_2)_2$—, —$(CH_2)_2O(CH_2)_2$—, —O—, —S—, —P(X)—, —C(=O)—, or —Si(R)$_2$—, where X and R are independently hydrogen, a substituted or unsubstituted $C_1$-$C_{20}$ alkyl, substituted or unsubstituted $C_6$-$C_{20}$ aryl, or a halogen atom; and n is 1 or 2.

In another aspect of the present invention, there is provided an organic electroluminescence device comprising an organic layer between a pair of electrodes, wherein the organic layer includes the binuclear organometallic complex.

BRIEF DESCRIPTION OF THE DRAWINGS

The above aspect and advantages of the present invention will become more apparent by describing in detail the preferred embodiments thereof with reference to the attached drawings.

DETAILED DESCRIPTION OF THE INVENTION

Figure 1:
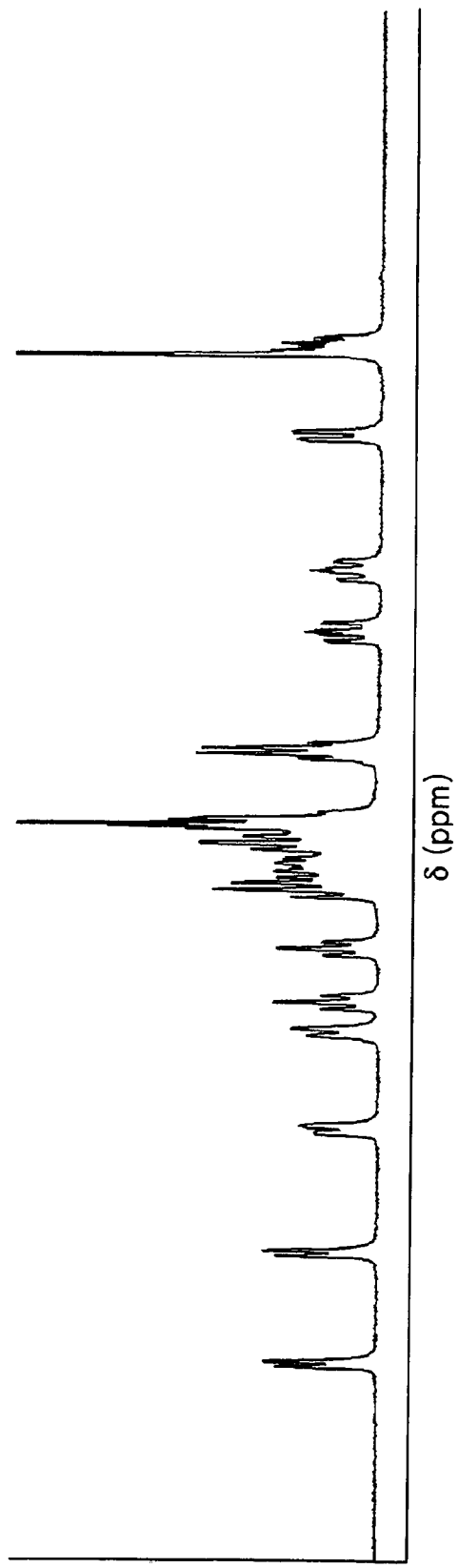
FIG. 1 is a view showing a $^1$H-NMR spectrum of a compound represented by formula 2 prepared in Example 1.

A binuclear organometallic complex represented by formula 1 according to the present invention increases an energy band gap between HOMO and triplet MLCT states, enabling blue electroluminescence. The increased energy band gap between HOMO level and triplet MLCT level allows coordination to a bulky ligand, leading to a twisted geometry. An increase in the energy gap is allowed by the introduction of a ligand capable of providing a strong ligand field exhibiting excellent σ-donor and π-donor capability. Examples of the ligand capable of performing such functions include organic phosphine, and a cyanide ion is one of the ligands capable of providing a strong ligand field and reducing the HOMO energy level, leading to a blue shift in the emission wavelength range.

The cyclometalating ligand (C^N) is one selected from the group consisting of ligands represented by the following formulas:

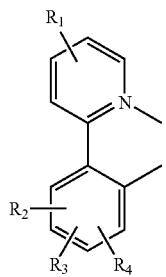
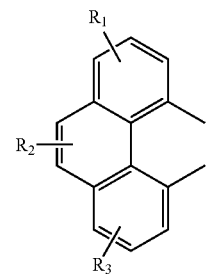
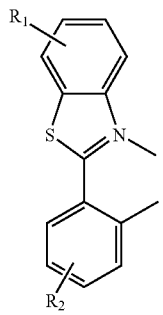
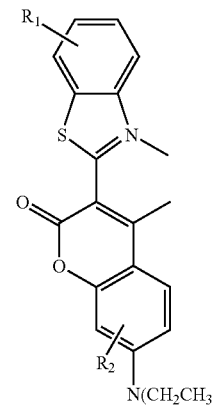
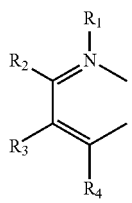
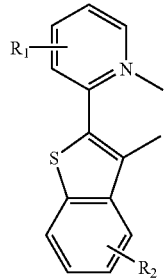
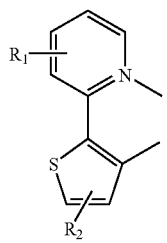
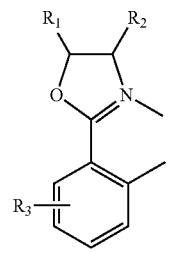
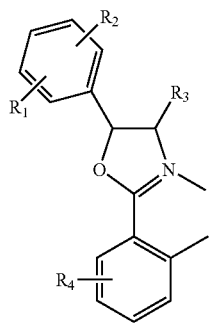
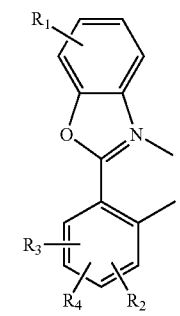

-continued

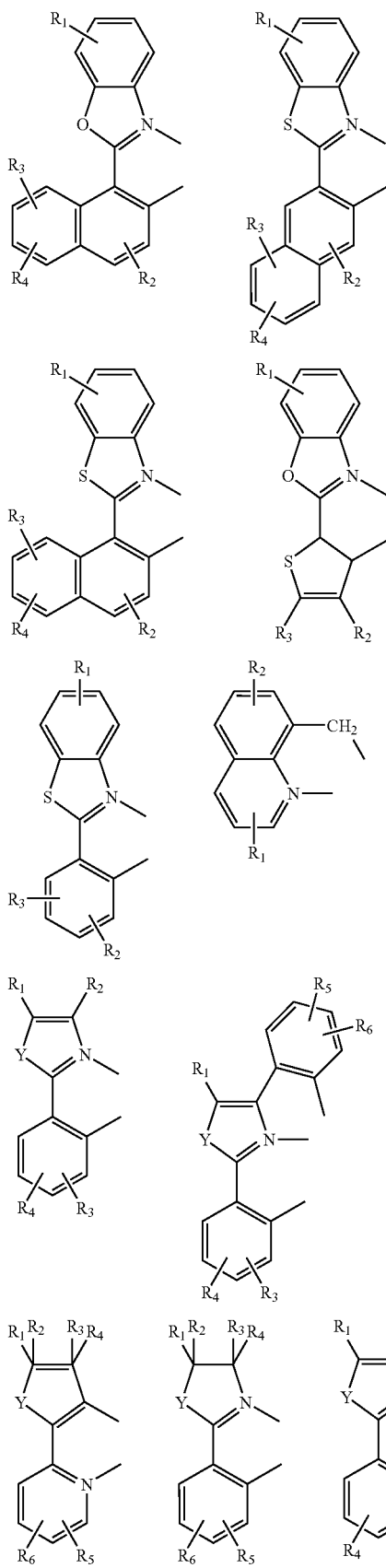
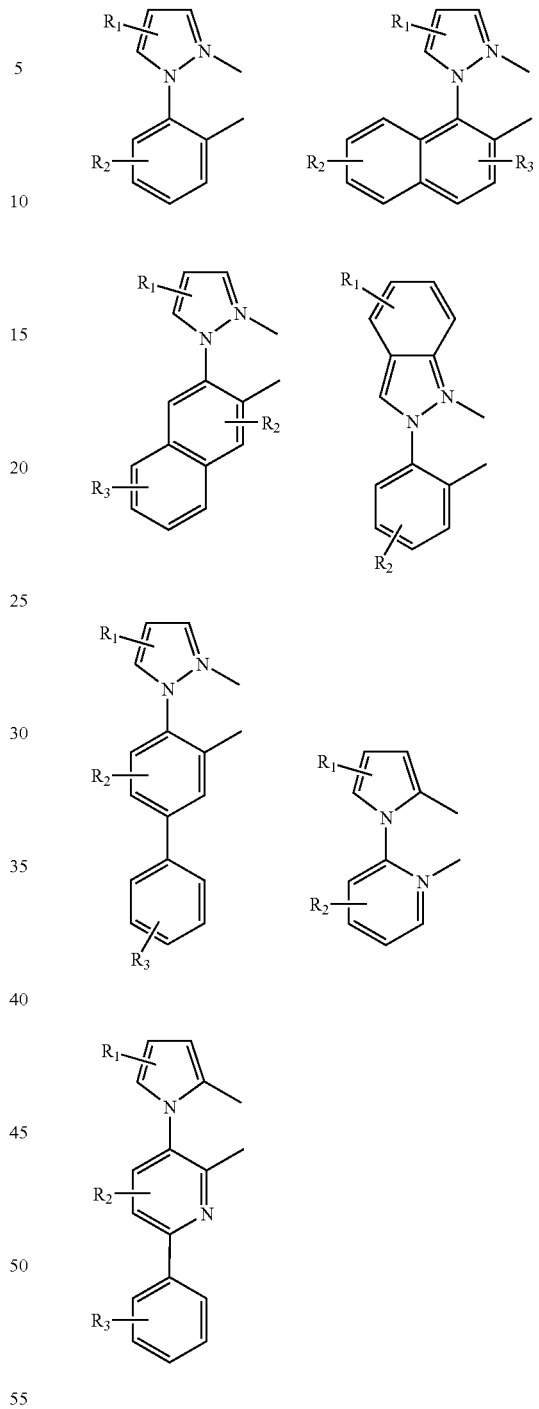

wherein $R_1$, $R_2$, $R_3$, $R_4$, $R_5$, and $R_6$ are independently a monosubstituted or multisubstituted substituent, and selected from the group consisting of hydrogen, halogen atom, $C_1$-$C_{20}$ alkyl, or $C_6$-$C_{20}$ aryl, silyl, phosphino, amino group;

Y is S, O, P, or NR where R is hydrogen or a $C_1$-$C_{20}$ alkyl group.

Specific examples of the binuclear organometallic complex of formula 1 include, but are not limited to, compounds represented by formulas 2 through 11:

[Formula 2]
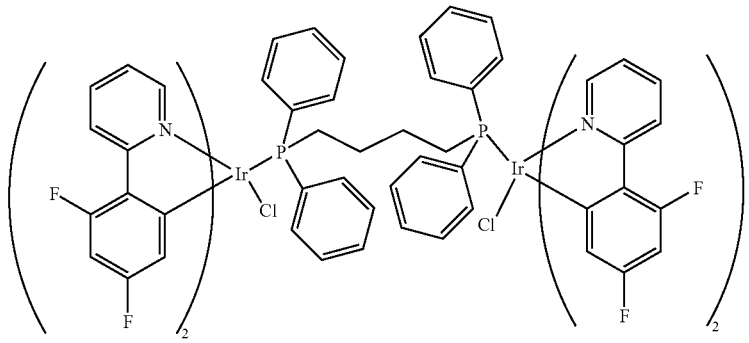
[Formula 3]
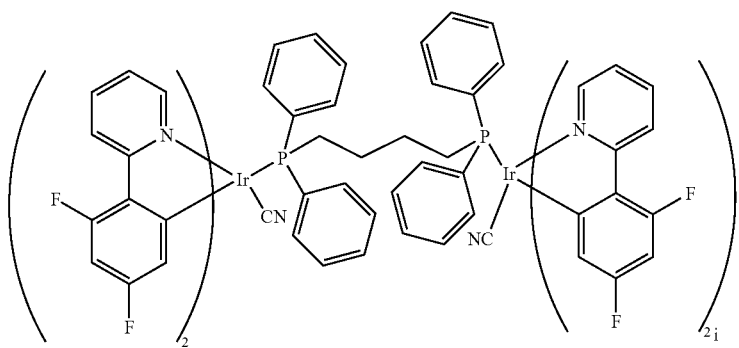
[Formula 4]
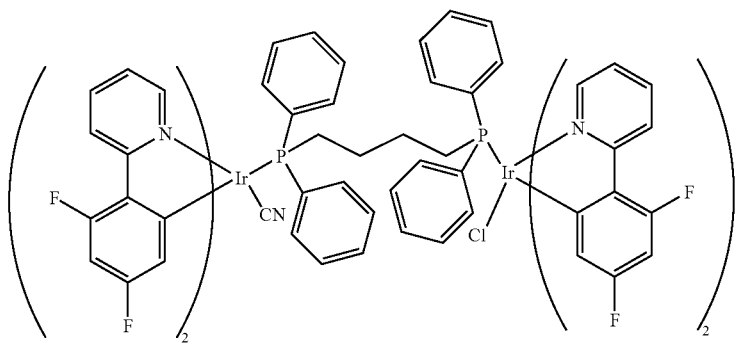
[Formula 5]
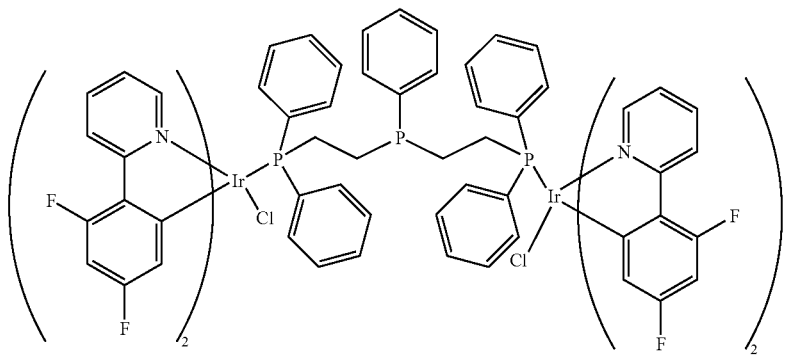

[Formula 6]
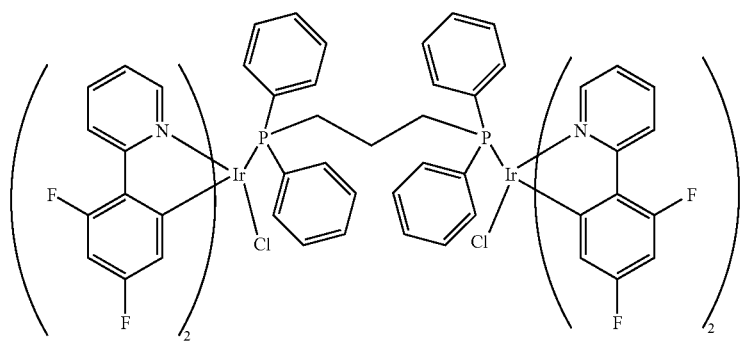
[Formula 7]
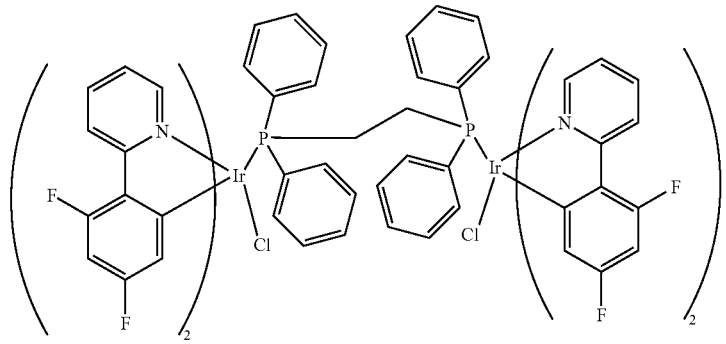
[Formula 8]
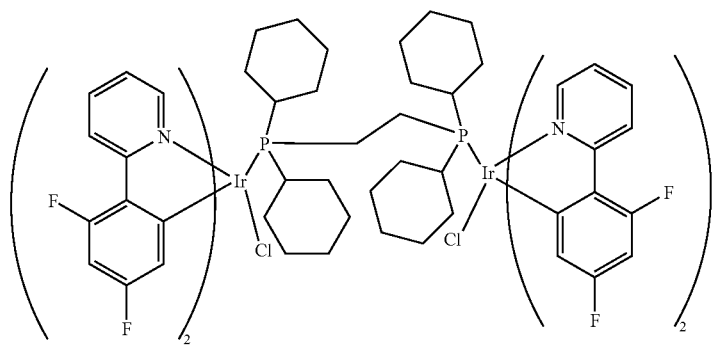
[Formula 9]
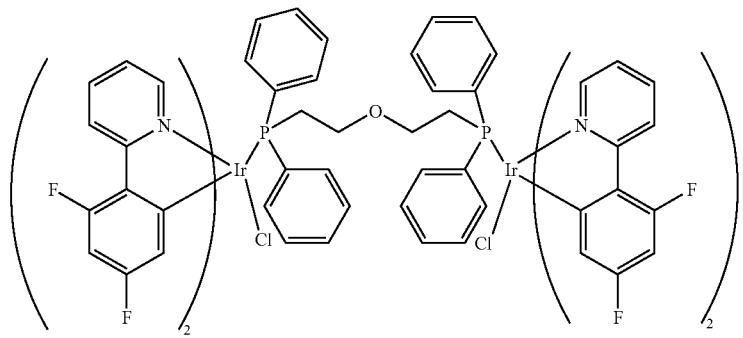

-continued

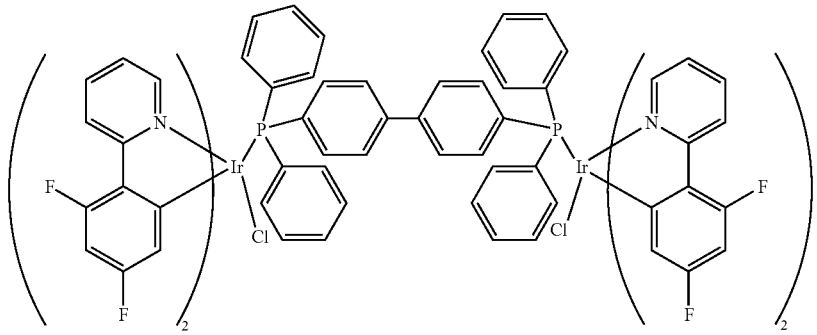

[Formula 10]

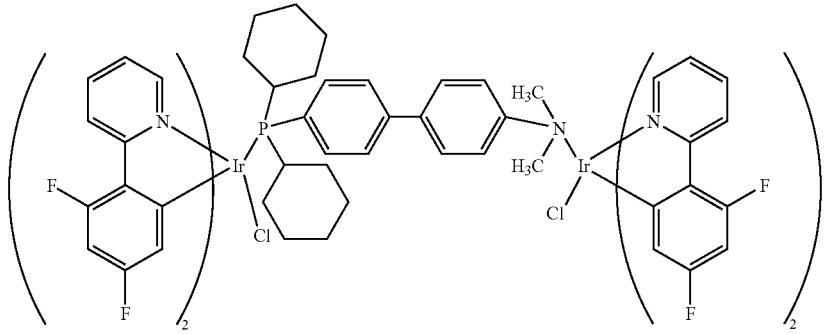

[Formula 11]

The organometallic complexes represented by formula 1 can be prepared by the method in which [Ir(C^N)$_2$Cl]$_2$ is used as a starting material for providing the cyclometalating moeity, as reported by Watts group. (See F. O. Garces, R. J. Watts, Inorg. Chem. 1988, (35), 2450).

The synthesis routes of the iridium complexes according to the examples of the present invention will now be described.

Referring to Reaction Scheme 1, [Ir(C^N)$_2$Cl]$_2$ as the starting material and PX$_1$X$_2$ZAX$_3$X$_4$ were mixed with a solvent such as methylene chloride, and stirred at room temperature for 2 to 48 hours, giving [Ir(C^N)$_2$Cl]$_2$ PX$_1$X$_2$ZAX$_3$X$_4$. The resulting product [Ir(C^N)$_2$Cl]$_2$ PX$_1$X$_2$ZAX$_3$X$_4$ was mixed with KCN in a solvent such as methylene chloride or methanol, and reacted at a temperature from room temperature to 50° C. for 1 to 6 hours, yielding a final product [Ir(C^N)$_2$CN]$_2$ PX$_1$X$_2$ZAX$_3$X$_4$, in which Cl bonded to iridium is substituted by CN. Another product of formula [Ir(C^N)$_2$CN] PX$_1$X$_2$ZAX$_3$X$_4$ [Ir(C^N)$_2$Cl] is also obtained, where one iridium is coordinated to a chloro group and another iridium is coordinated to a cyano group.

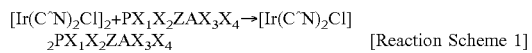
[Reaction Scheme 1]

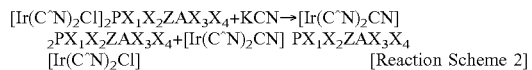
[Reaction Scheme 2]

wherein X$_1$ through X$_4$, A and Z are as defined above.

The organometallic complex according to the present invention can emit light not only in the blue range but also in various wavelength ranges by the structural alteration of the ligands.

The organic electroluminescent device according to the present invention may be manufactured by forming an organic layer, particularly a light-emitting layer, using the organometallic complex represented by formula 1. The organometallic complex represented by formula 1 is very advantageously used as a phospholuminescent dopant material, which is a material for forming the light-emitting layer, and exhibits an excellent emission efficiency in the blue range.

When the organometallic complex represented by formula 1 is used as a phospholuminescent dopant, the organic layer may further comprises at least one material selected from the group consisting of at least one high molecular host, a mixture of a high molecular host and a low molecular host, a low molecular host, and non-luminous high molecular matrix. As the high molecular host, the low molecular host and the non-luminous high molecular matrix, any useful materials known in the art as materials for forming a light-emitting layer of an organic electroluminescent device can be used. Typical examples of the high molecular host include, but are not limited to, poly(vinylcarbazole) (PVK), polyfluorene and the like, typical examples of the low molecular host include, but are not limited to, CBP(4,4'-N,N'-dicarbazole-biphenyl), 4,4'-bis[9-(3,6-biphenylcarbazolyl)]-1-1,1'-biphenyl{4,4'-bis[9-(3,6-biphenylcarbazolyl)]-1-1,1'-biphenyl}, 9,10-bis[(2',7'-t-butyl)-9',9''-spirobifluorenylanthracene, tetrafluorene and the like. Typical examples of the non-luminous high molecular matrix include, but are not limited to, polymethylmethacrylate, polycarbonate, polystyrene and the like.

Preferably, the organometallic complex represented by formula 1 may be used in an amount of about 1 to 30 parts per 100 by weight based on the total weight, i.e., 100 parts by weight for the total weight of the light-emitting layer forming material. Examples of methods useful to introduce the organometallic complex into, onto, or with the light-emitting layer include vacuum deposition, sputtering, printing, coating, ink-jet printing, electron-beam application, and deposition or lamination techniques.

The organometallic complex represented by formula 1 can induce white electroluminescence when combined with green or red luminescent materials.

The thickness of the individual organic layer may preferably be in a range of about 10 to 100 nm. The term "organic layer" used herein means a layer made of an organic compound formed between a pair of electrodes in an organic electroluminescent device, for example, a light-emitting layer, an electron transport layer, or a hole transport layer.

The organic electroluminescent device may have a known structure selected from the group consisting of anode/light-emitting layer/cathode, anode/buffer layer/light-emitting layer/cathode, anode/hole transport layer/light-emitting layer/cathode, anode/buffer layer/hole transport layer/light-emitting layer/cathode, anode/buffer layer/hole transport layer/light-emitting layer/electron transport layer/cathode, and anode/buffer layer/hole transport layer/light-emitting layer/hole blocking layer/cathode, but is not particularly limited to these structures.

The buffer layer may use any conventional buffer layer material, or any other suitable buffer material. For example, one may use copper phthalocyanine, polythiophene, polyaniline, polyacetylene, polypyrrole, polyphenylene vinylene, or derivatives thereof in the buffer layer.

Similarly, the hole transport layer material may be a conventional material or any other suitable material. For example, one may use polytriphenylamine is used.

The electron transport layer may include any conventional material or other suitable material for such a layer. For example, polyoxadiazole may be used in this layer.

Similarly, the hole blocking layer material may be any conventional material or other suitable material for such a layer. For example, one may use BCP, TAZ, TPBI, or Balq for this layer.

The organic electroluminescence device according to the present invention can be manufactured in accordance with the conventional apparatus and methods in the art without any special limitations.

The binuclear iridium complex can emit light of wavelengths in a range from 400 to 650 nm. LEDs using such organometallic complexes can be used in applications such as light sources for a full color display, backlighting, signboards, optical communication, indoor decoration, and the like.

The present invention will now be described in more detail with reference to the following examples. However, these examples are given for the purpose of illustration and not of limitation.

EXAMPLE 1

Synthesis of [Ir(F$_2$ppy)$_2$Cl]$_2$P(Ph)$_2$(CH$_2$)$_4$P(Ph)$_2$ Represented by Formula 2

To 0.1 mmol of iridium complex [Ir(F$_2$ppy)$_2$Cl]$_2$ represented by the following formula, dissolved in 10 mL methylene chloride, was slowly added 0.1 mmol of P(Ph)$_2$(CH$_2$)$_4$P(Ph)$_2$ (BDP), and stirred under a nitrogen atmosphere at room temperature for 2 hours.

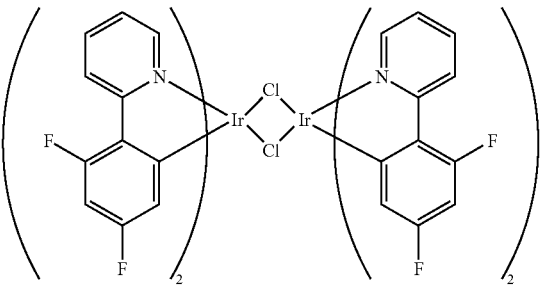

Figure 2:
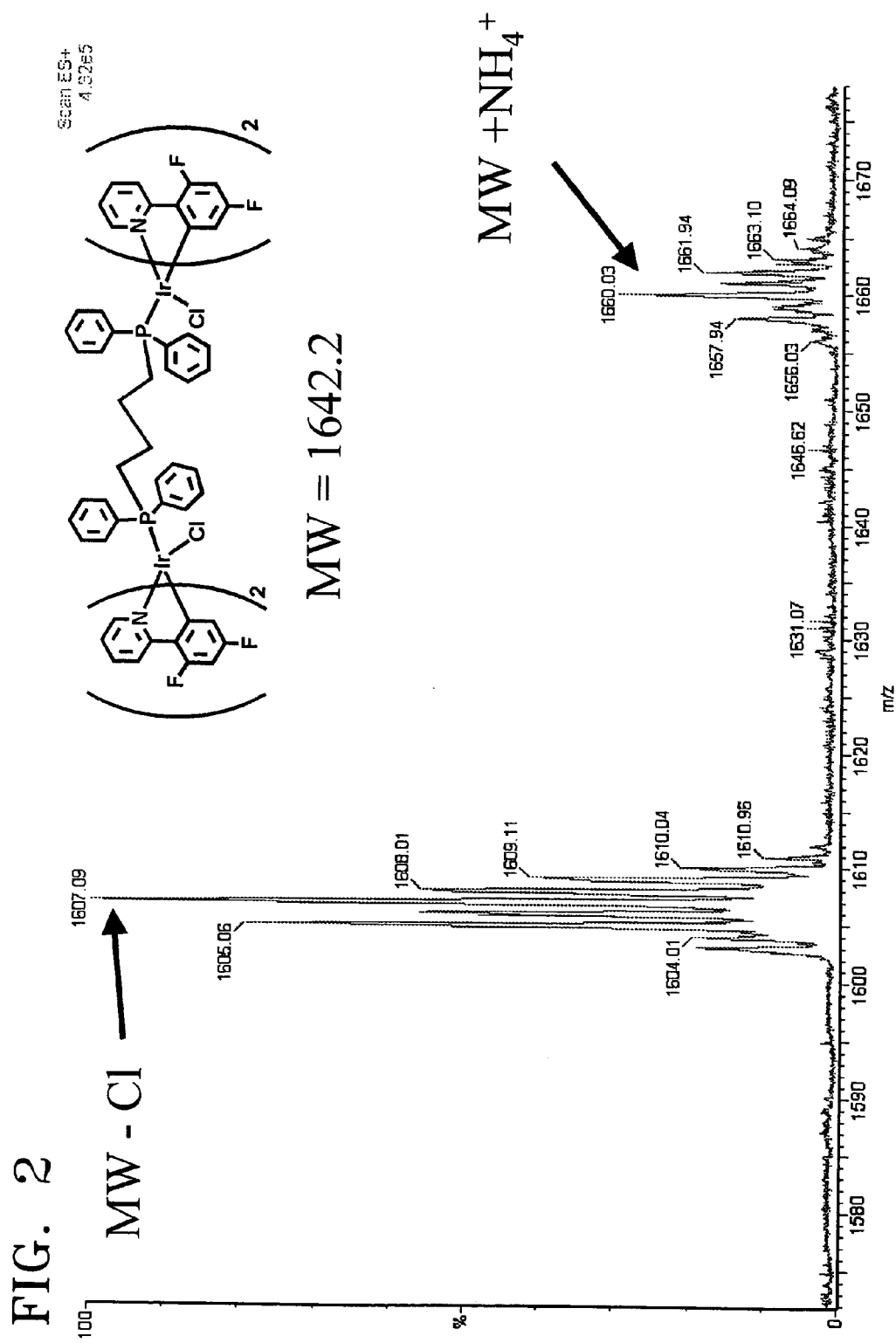
FIG. 2 is a view showing a mass spectrum of the compound represented by formula 2 prepared in Example 1 by mass spectrometry.

Then, the reaction mixture was distilled under reduced pressure to remove the solvent, acquiring a lemon color solid. The acquired solid was isolated by silica gel column chromatography using a mixed solvent consisting of methylene chloride and acetone in a volumetric ratio of 10:1, dissolved in 5 mL of methylene chloride, and reprecipitated by hexane as a yellow precipitate, followed by filtering and drying. This procedure was repeatedly performed three times, yielding a final product represented by formula 2, that is, [Ir(F$_2$ppy)$_2$Cl]$_2$P(Ph)$_2$(CH$_2$)$_4$P(Ph)$_2$. The composition and structure of the final product were identified through mass spectrometry and $^1$H-NMR spectroscopy. FIG. 1 is a view showing the $^1$H-NMR spectrum of the compound represented by formula 2 prepared in Example 1, and FIG. 2 is a view showing the mass spectrum thereof.

The structure of the compound represented by formula 2, as identified through $^1$H NMR spectroscopy, gives the following $^1$H NMR resonances: (300 MHz, CD$_2$Cl$_2$), ppm: 9.24 (d, 1H), 8.81 (d, 1H), 8.32 (d, 1H), 7.96 (d, 1H), 7.84 (t, 1H), 7.62 (t, 1H), 7.44-7.06 (m, 10H), 6.85 (d, 2H), 6.39 (t, 1H), 6.15 (t, 1H), 5.63 (d, 1H), 5.27 (t, 1H), 2.18 (b, 1H), 1.51 (b, 1H), 1.17 (b, 2H).

The obtained compound represented by formula 2 was tested for emission characteristics in the following manners.

First, the compound represented by formula 2 was dissolved in methylene chloride to prepare a 10$^{-5}$ M solution, and then emission characteristics of the compound in a solution state were examined.

Next, 6% by weight of the compound represented by formula 2 and 94% by weight of polymethylmethacrylate (PMMA) were dissolved in a solvent to be fabricated into a film. Then, the emission characteristics of the compound being in a film state were examined.

The results showed that the compound represented by formula 2 had an emission wavelength peak at 462 nm with a shoulder at 488 nm in the solution state, and that the compound had substantially the same emission profile in the film state.

The CIE color coordinate (x, y) of the compound was (0.15, 0.26).

EXAMPLE 2

Synthesis of [Ir(F$_2$ppy)$_2$CN]$_2$P(Ph)$_2$(CH$_2$)$_4$P(Ph)$_2$ Represented by Formula 3 and [Ir(F$_2$ppy)$_2$Cl]-P(Ph)$_2$(CH$_2$)$_4$P(Ph)$_2$-[Ir(F$_2$ppy)$_2$CN] Represented by Formula 4

0.1 mmol of [Ir(F$_2$ppy)$_2$Cl]$_2$BDP represented by formula 2 was dissolved in 10 mL methylene chloride under a nitrogen atmosphere, and then added to 10 mmol of KCN dissolved in 15 mL of methanol. The reaction mixture was stirred under a nitrogen atmosphere at room temperature for 5 hours, and the solvent was removed by distillation under reduced pressure. Then, the reaction product was isolated by silica gel column chromatography using a mixed solvent consisting of methylene chloride, acetone and hexane in a volumetric ratio of 9:1:3. The column chromatography yielded 3 bands. Precipitates were obtained from each eluate passing through the column by the same method as in Example 1. The first eluate was unreacted [Ir($F_2$ppy)$_2$Cl]$_2$ BDP, the second eluate was [Ir($F_2$ppy)$_2$ Cl]-BDP-[Ir($F_2$ppy)$_2$ CN] represented by formula 4, and the third eluate was [Ir($F_2$ppy)$_2$ CN]$_2$BDP represented by formula 3. The compositions and structures of the final products were identified through mass spectrometry and $^1$H-NMR spectroscopy.

The structure of the compound represented by formula 3, as identified through $^1$H NMR spectroscopy, gives the following $^1$H NMR resonances: (300 MHz, CD$_2$Cl$_2$), ppm: 8.97 (d, 1H), 8.68 (d, 1H), 8.38 (d, 1H), 8.01 (d, 1H), 7.86 (t, 1H), 7.61 (t, 1H), 7.52-7.06 (m, 10H), 6.88 (d, 1H), 6.73 (t, 1H), 6.45 (t, 1H), 6.22 (t, 1H), 5.59 (d, 1H), 5.36 (t, 1H), 2.1 (b, 1H), 1.69 (b, 1H), 1.23 (b, 2H).

The structure of the compound represented by formula 4, as identified through $^1$H NMR spectroscopy, gives the following $^1$H NMR resonances: (300 MHz, CD$_2$Cl$_2$), ppm: 9.20 (d, 1H), 8.96 (d, 1H), 8.82 (t, 1H), 8.69 (d, 1H), 8.35 (t, 2H), 8.00 (t, 2H), 7.86 (d, 2H), 7.62 (t, 2H), 7.51-7.02 (m, 18H), 6.96-6.63 (m, 4H), 6.41 (m, 2H), 6.19 (m, 2H), 5.69-5.39 (t, 1H), 5.26 (d, 1H), 2.36-1.96 (m, 2H), 1.81-1.37 (m, 4H), 1.20-0.98 (m, 2H).

Molecular weights of the compounds represented by formulas 3 and 4 were confirmed through ESI mass spectrometry.

The emission characteristics of the compounds represented by formulas 3 and 4, that is, [Ir($F_2$ppy)$_2$CN]$_2$BDP and [Ir($F_2$ppy)$_2$Cl]-BDP-[Ir($F_2$ppy)$_2$CN] were evaluate, and the results thereof are as follows.

According to the evaluation results, [Ir($F_2$ppy)$_2$CN]$_2$BDP represented by formula 3 had emission wavelength peaks at 450 nm and 477 nm. The CIE color coordinate (x, y) of the compound was (0.14, 0.18).

The compound represented by formula 4 had an emission wavelength peak at 461 nm with a shoulder at 488 nm in a solution state and showed substantially the same emission profile with that in a film state. The CIE color coordinate (x, y) of the compound was (0.14, 0.22).

EXAMPLE 3

Synthesis of [Ir($F_2$ppy)$_2$ Cl]$_2$P(Ph)$_2$(CH$_2$)$_2$P(Ph)(CH$_2$)$_2$ Represented by Formula 5

0.1 mmol of [Ir($F_2$ppy)$_2$ Cl]$_2$ represented by the following formula was dissolved in 10 mL of methylene chloride under a nitrogen atmosphere, and 0.1 mmol of P(Ph)$_2$(CH$_2$)$_2$P(Ph)(CH$_2$)$_2$P(Ph)$_2$(3P) was added thereto.

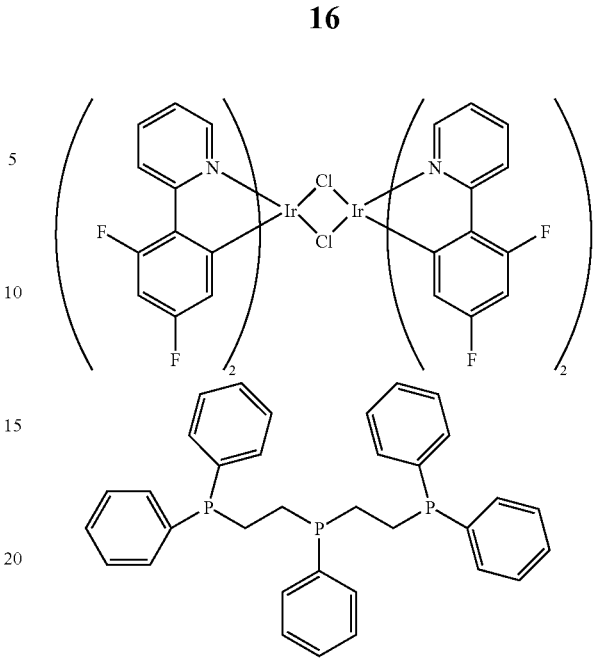

The reaction mixture was stirred at room temperature for 24 hours and then the solvents were removed under reduced pressure, and a yellow colored solid was obtained. The acquired solid was passed through a silica gel column using ether as the eluent, followed by the removal the solvent. Thereafter, the resultant product was passed through a silica gel column using a mixed solvent consisting of methylene chloride, acetone and hexane in a volumetric ratio of 12:1:3, acquiring a yellow solid after the solvent evaporation. The solid was precipitated upon the addition of hexane to a methylene chloride solution. The structure of the compound represented by formula 5, is identified through $^1$H NMR spectroscopy. The result was, at $^1$H NMR (300 MHz, CD$_2$Cl$_2$), ppm: 9.31 (d, 1H), 9.25 (d, 1H), 8.50 (d, 1H), 8.28 (d, 1H), 7.85 (d, 1H), 7.62 (t, 1H), 7.57-6.97 (m, 10H), 6.42-6.10 (m, 3H), 5.84 (t, 2H), 5.25 (d, 1H), 5.09 (t, 1H), 2.60-2.42 (m, 2H), 1.8 (t, 2H).

The molecular weight of the compound represented by formula 5 was confirmed through ESI mass spectrometry.

According to the evaluation results, the compound represented by formula 5 had an emission wavelength peak at 460 nm in a 10$^{-5}$ M methylene chloride solution state and showed substantially the same emission profile with that in a film state. The CIE color coordinate (x, y) of the compound was (0.14, 0.22).

EXAMPLE 4

Synthesis of [Ir($F_2$ppy)$_2$Cl]$_2$ P(Ph)$_2$(CH$_2$)$_3$P(Ph)$_2$ Represented by Formula 6

P(Ph)$_2$(CH$_2$)$_3$P(Ph)$_2$ was reacted by substantially the same method as in Example 1 to synthesize the compound represented by formula 6.

The structure of the compound represented by formula 6, is identified through $^1$H NMR spectroscopy: $^1$H NMR (300 MHz, CD$_2$Cl$_2$), ppm: 9.26 (dd, 2H), 8.55 (t, 2H), 8.28 (d, 2H), 7.88 (dd, 2H), 7.69 (t, 2H), 7.35-6.73 (m, 22H), 6.39 (t, 4H), 6.27 (t, 2H), 5.62 (dd, 2H), 5.28 (t, 2H), 2.66-2.35 (b, 2H), 1.87 (t, 1H), 1.65 (t, 1H), 1.42-1.02 (b, 2H).

The molecular weight of the compound represented by formula 6 was confirmed through ESI mass spectrometry.

EXAMPLE 5

Synthesis of [Ir(F$_2$ppy)$_2$Cl]$_2$P(Ph)$_2$(CH$_2$)$_2$P(Ph)$_2$ Represented by Formula 7

P(Ph)$_2$(CH$_2$)$_2$P(Ph)$_2$ was reacted by substantially the same method as in Example 1 to synthesize the compound represented by formula 7.

The structure of the compound represented by formula 7, is identified through $^1$H NMR spectroscopy. $^1$H NMR (300 MHz, CD$_2$Cl$_2$), ppm: 9.55 (d, 1H), 8.67 (d, 1H), 8.22 (d, 1H), 8.07-7.86 (m, 3H), 7.80 (d, 1H), 7.69-7.25 (m, 7H), 7.16 (d, 1H), 6.97 (t, 3H), 6.70 (t, 1H), 6.26 (t, 3H), 5.17 (d, 1H), 5.03 (t, 1H), 2.03 (b, 2H), 1.48 (b, 1H).

The molecular weight of the compound represented by formula 7 was confirmed through ESI mass spectrometry.

EXAMPLE 6

Synthesis of [Ir(F$_2$ppy)$_2$ Cl]$_2$ P(cyclohexyl)$_2$(CH$_2$)$_2$P(cyclohexyl)$_2$ Represented by Formula 8

P(cyclohexyl)$_2$(CH$_2$)$_2$P(cyclohexyl)$_2$ was reacted by substantially the same method as in Example 1 to synthesize the compound represented by formula 8.

Figure 3:
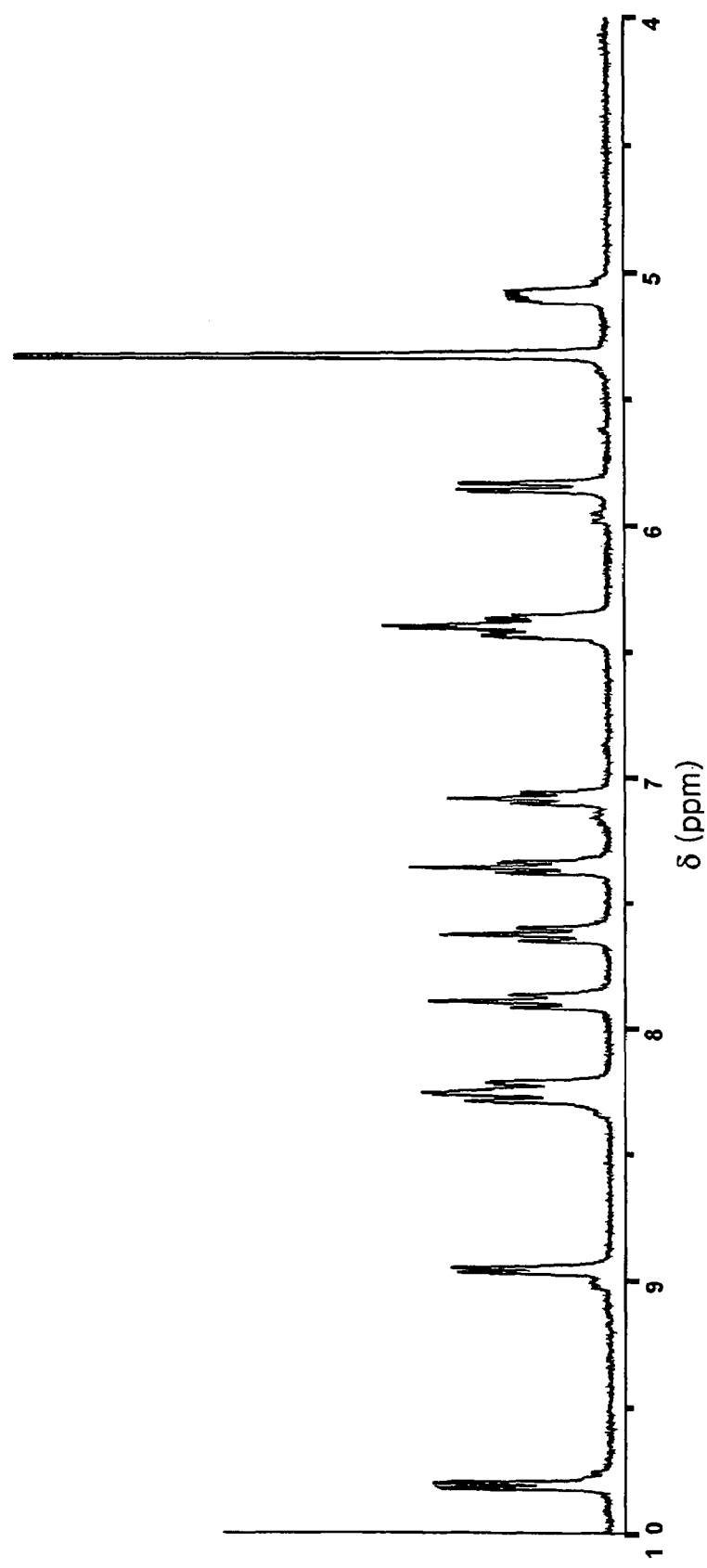
FIG. 3 is a view showing a $^1$H-NMR spectrum of a compound represented by formula 8 prepared in Example 6.
Figure 4:
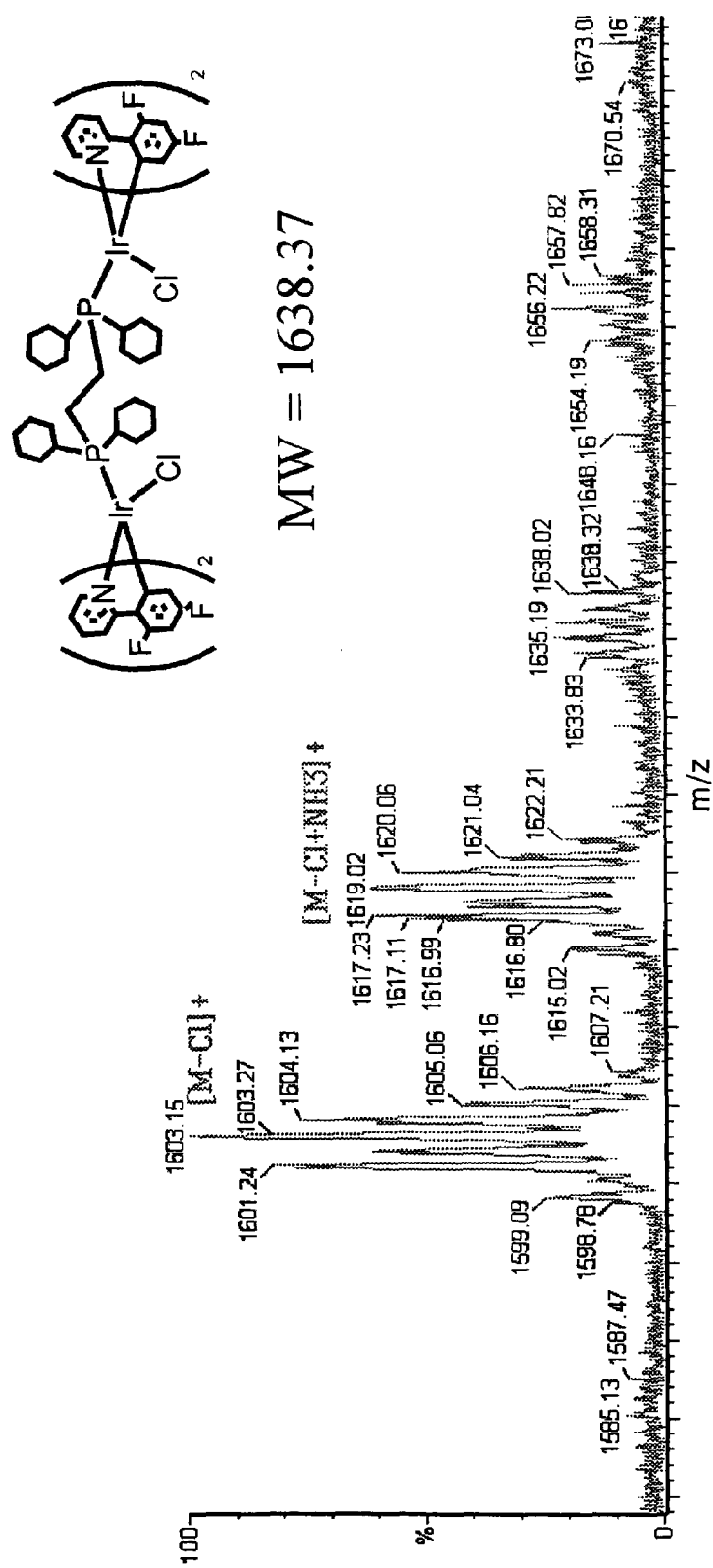
FIG. 4 is a view showing a mass spectrum of the compound represented by formula 6 prepared in Example 8 by mass spectrum.

FIG. 3 is a view showing a $^1$H-NMR spectrum of the compound represented by formula 8 prepared in Example 6, and FIG. 4 is a view showing a mass spectrum thereof.

The structure of the compound represented by formula 8, is identified through $^1$H NMR spectroscopy. $^1$H NMR (300 MHz, CD$_2$Cl$_2$), ppm: 9.8 (d, 1H), 8.95 (d, 1H), 8.25 (t, 2H), 7.89 (t, 1H), 7.62 (t, 1H), 7.35 (t, 1H), 7.08 (t, 1H), 6.39 (t, 2H), 5.84 (d, 1H), 5.08 (t, 1H), 2.37 (b, 1H), 2.24 (b, 1H), 2.07-1.38 (m, 12H), 1.23-0.98 (m, 4H), 0.92-0.63 (m, 6H).

The molecular weight of the compound represented by formula 8 was confirmed through ESI mass spectrometry.

EXAMPLE 7

Synthesis of [Ir(F$_2$ppy)$_2$Cl]$_2$P(Ph)$_2$(CH$_2$)$_2$O(CH$_2$)$_2$P(Ph)$_2$ Represented by Formula 9

P(Ph)$_2$(CH$_2$)$_2$O(CH$_2$)$_2$P(Ph)$_2$ was reacted by substantially the same method as in Example 1 to synthesize the compound represented by formula 9.

The structure of the compound represented by formula 9, is identified through $^1$H NMR spectroscopy. $^1$H NMR (300 MHz, CD$_2$Cl$_2$), ppm: 9.18 (d, 1H), 8.73 (d, 1H), 8.30 (d, 1H), 7.88 (d, 1H), 7.79 (t, 1H), 7.58 (t, 1H), 7.42-7.08 (m, 10 H), 6.82 (d, 2H), 6.34 (t, 1H), 6.08 (t, 1H), 5.60 (d, 1H), 5.24 (t, 1H), 2.08 (b, 1H), 1.46 (b, 1H), 1.17 (b, 2H).

The molecular weight of the compound represented by formula 9 was confirmed through ESI mass spectrometry.

EXAMPLE 8

Synthesis of [Ir(F$_2$ppy)$_2$Cl]$_2$P(Ph)$_2$(Ph)$_2$P(Ph)$_2$ Represented by Formula 10

P(Ph)$_2$(Ph)$_2$P(Ph)$_2$ was reacted by substantially the same method as in Example 1 to synthesize the compound represented by formula 10.

The structure of the compound represented by formula 10, is identified through $^1$H NMR spectroscopy. $^1$H NMR (300 MHz, CD$_2$Cl$_2$), ppm: 9.76 (d, 1H), 9.54 (d, 1H), 8.36-8.00 (m, 4H), 7.61 (d, 2H), 6.79 (t, 3H), 5.73 (d, 1H), 5.07 (d, 1H).

The molecular weight of the compound represented by formula 10 was confirmed through ESI mass spectrometry.

EXAMPLE 9

Synthesis of [Ir(F$_2$ppy)$_2$Cl]$_2$P(cyclohexyl)$_2$(Ph)$_2$N(CH$_3$)$_2$ Represented by Formula 11

P(cyclohexyl)$_2$(Ph)$_2$N(CH$_3$)$_2$ was reacted by substantially the same method as in Example 1 to synthesize the compound represented by formula 11.

HOMO and LUMO energy levels and emission characteristics of the compounds represented by formulas 2 through 11 are summarized in Table 1.

TABLE 1

| Formula | HOMO (eV) | (max(nm)) in solution | (max(nm)) in film | LUMO (eV) | CIE (x,y) | Decomposition temperature |
|---|---|---|---|---|---|---|
| 2 | 6.20 | 462 | 463 | 2.85 | (0.15, 0.26) | 300 |
| 3 | 6.32 | 450, 477 | 450, 477 | 3.57 | (0.14, 0.18) | 266 |
| 4 | 6.26 | 461, 488 | 462 | 2.91 | (0.14, 0.22) | 250 |
| 5 | 6.40 | 460 | 460 | 2.96 | (0.14, 0.22) | 290 |
| 6 | 6.15 | 460 | 461 | 3.46 | (0.14, 0.21) | 315 |
| 7 | 6.11 | 460 | 461 | 3.42 | (0.14, 0.20) | 310 |
| 8 | 6.12 | 468 | 467 | 2.86 | (0.14, 0.26) | 305 |
| 9 | — | 462 | 461 | — | (0.16, 0.28) | 280 |
| 10 | — | 494 | 498 | — | (0.19, 0.51) | 295 |
| 11 | — | 480 | 482 | — | (0.15, 0.27) | 290 |

EXAMPLE 10

Manufacture of Electroluminescent Device 20 nm of PEDOT in isopropyl alcohol was spin coated on a precleaned ITO coated glass substrate to make a hole injecting and transporting layer (HIL, HTL) and then baked at 120° C. for 1 h. Next, 0.015 g of PMMA, 0.0226 g of mCP and 0.0025 of the dopant [(F$_2$ppy)Ir CN]$_2$ BDP were dissolved in 3.96 g of dichloroethane so as to make a 6% doped film of the dopant in PMMA and MCP. The PMMA to mCP ratio was 40:60. The solution was filtered and spin coated on the PEDOT-PS film to make a 40 nm film of the emissive layer (EL) followed by baking at 60° C. for 2 h in glove box. Then 20 nm hole blocking layer (HBL) of BCP followed by 40 nm of the electron injecting layer (EIL) Alq$_3$ were vapor deposited on the emissive layer. Subsequently 0.8 nm of LiF and 100 nm of Al were deposited on Alq$_3$, thereby finally completing an organic electroluminescence device.

The device was tested for the EL performance and was found to furnish an efficiency of 2 cd/A with the emission of blue light. The CIE color coordinates (CIE) are (0.21, 0.34). Similar device was fabricated for the dopants, [(F$_2$ppy)Ir CN]$_2$ CHDP. The efficiencies and CIE color coordinates of the devices are 1.34 cd/A and (0.24, 0.38), respectively.

The binuclear organometallic complex represented by formula 1 can efficiently emit light of wavelengths from a blue range to a red range from the triplet MLCT state. The organometallic complex is suitably used for forming an organic layer of the organic electroluminescent device, and provides a luminescence maximum emission in the wavelength range of 400-650 nm.

Although the above examples may be useful in understanding the invention, they are not intended to describe or limit the scope of the invention. The scope of the invention is properly understood with reference to the claims.

What is claimed is:

1. A binuclear organometallic complex represented by formula 1:

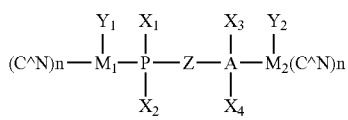

wherein (C^N) represents a cyclometalating ligand bonded to M through nitrogen (N) and carbon (C), and represents the following structure,

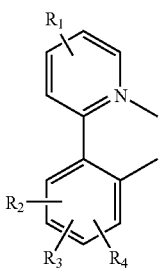

A is a phosphorus (P) or nitrogen (N);

Z is a substituted or unsubstituted C$_1$-C$_{20}$ alkylene, substituted or unsubstituted C$_6$-C$_{20}$ arylene, —(CH$_2$)$_2$P(C$_6$H$_5$)(CH$_2$)$_2$— or —(CH$_2$)$_2$O(CH$_2$)$_2$—;

X$_1$, X$_2$, X$_3$ and X$_4$ are independently substituted or unsubstituted C$_1$-C$_{20}$ alkyl, substituted or unsubstituted C$_6$-C$_{20}$ aryl or a substituted or unsubstituted C$_4$-C$_{20}$ cycloalkyl;

M$_1$ and M$_2$ are Ir;

Y$_1$ and Y$_2$ are independently a halogen atom or CN;

R$_1$, R$_2$, R$_3$ and R$_4$ are independently a monosubstituted or multisubstituted substituent, and selected from the group consisting of hydrogen, halogen atom, C$_1$-C$_{20}$ alkyl, C$_6$-C$_{20}$ aryl, silyl or amino group; and n is 1 or 2.

2. The binuclear organometallic complex of claim 1, which is a compound represented by formula 2:

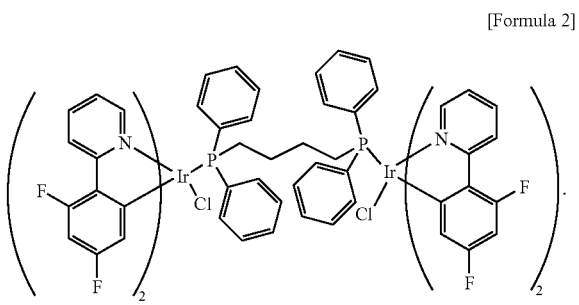

[Formula 2]

3. The binuclear organometallic complex of claim 1, which is a compound represented by formula 3:

[Formula 3]

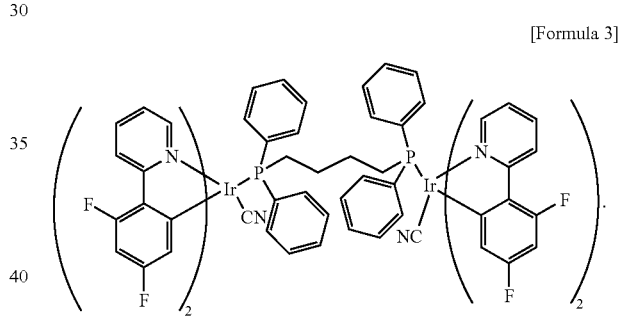

4. The binuclear organometallic complex of claim 1, which is a compound represented by formula 4:

[Formula 4]

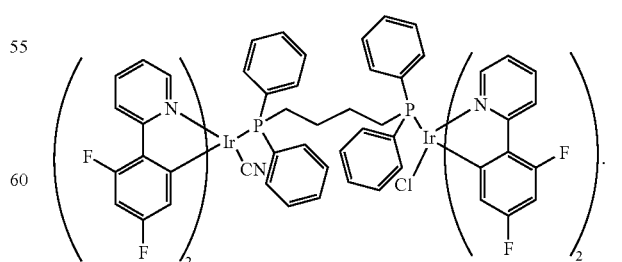

5. The binuclear organometallic complex of claim 1, which is a compound represented by formula 5:

[Formula 5]

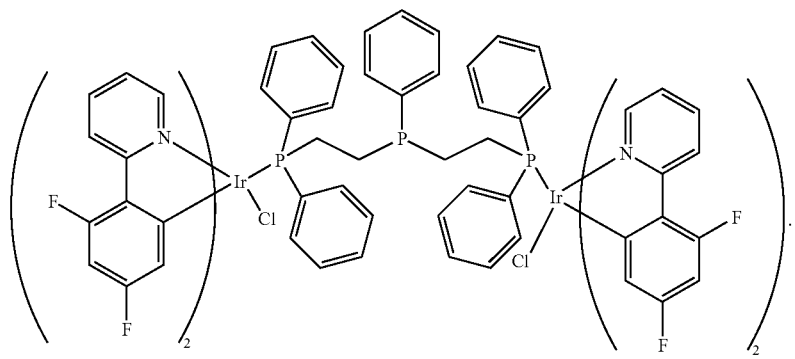

6. The binuclear organometallic complex of claim 1, which is a compound represented by formula 6:

[Formula 6]

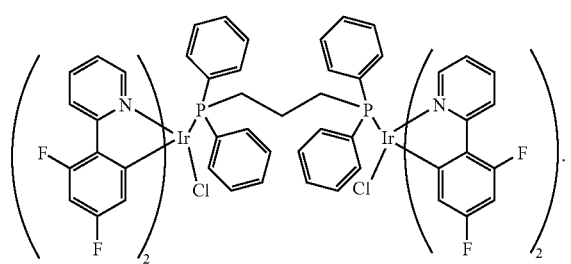

7. The binuclear organometallic complex of claim 1, which is a compound represented by formula 7:

[Formula 7]

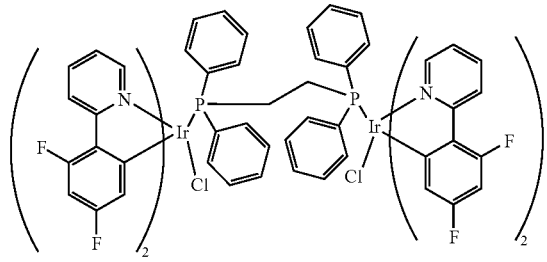

8. The binuclear organometallic complex of claim 1, which is a compound represented by formula 8:

[Formula 8]

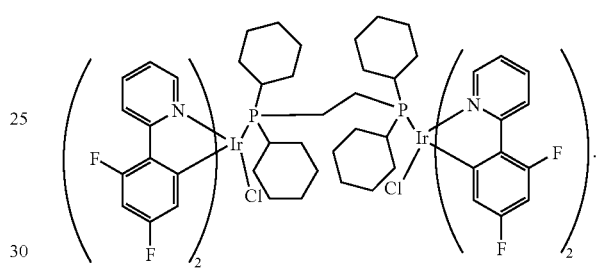

9. The binuclear organometallic complex of claim 1, which is a compound represented by formula 9:

[Formula 9]

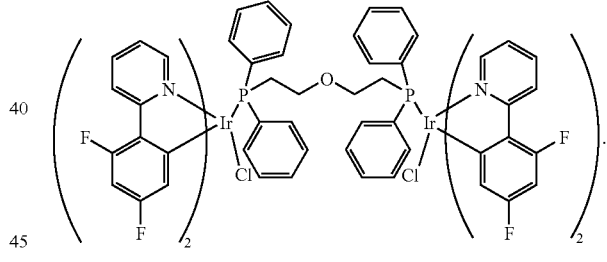

10. The binuclear organometallic complex of claim 1, which is a compound represented by formula 10:

[Formula 10]

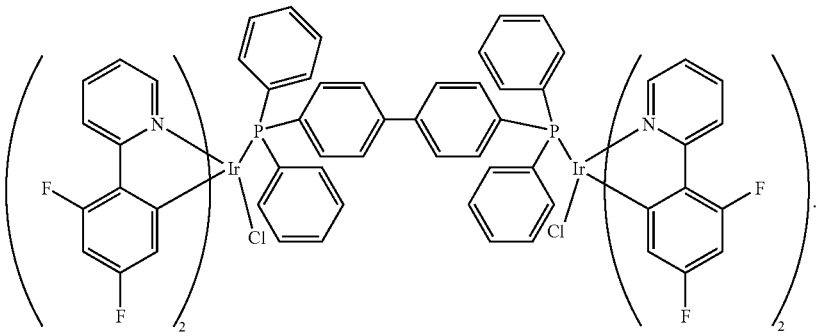

11. The binuclear organometallic complex of claim 1, which is a compound represented by formula 11:

[Formula 11]

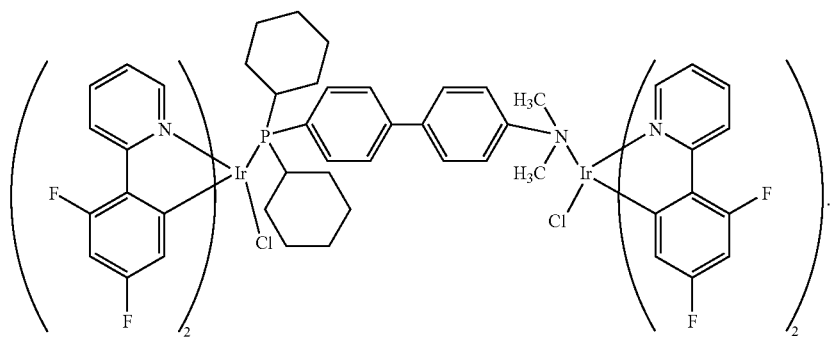

12. An organic electroluminescent device comprising an organic layer between a pair of electrodes, wherein the organic layer comprises the binuclear organometallic complex represented by formula 1:

[Formula 1]

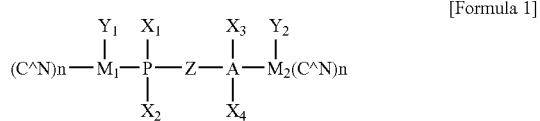

wherein (C^N) represents a cyclometalating ligand bonded to M through nitrogen (N) and carbon (C);

$M_1$ and $M_2$ are independently Ru, Rh, Pt, Os or Ir;

$X_1$, $X_2$, $X_3$, and $X_4$ are independently a substituted or unsubstituted $C_1$-$C_{20}$ alkyl, substituted or unsubstituted $C_1$-$C_{20}$ alkoxy, substituted or unsubstituted $C_{2\text{-}C20}$ alkenyl, substituted or unsubstituted $C_2$-$C_{20}$ alkynyl, a substituted or unsubstituted $C_4$-$C_{20}$ cycloalkyl, substituted or unsubstituted $C_6$-$C_{20}$ aryl, substituted or unsubstituted $C_2$-$C_{20}$ heteroaryl, substituted or unsubstituted $C_6$-$C_{20}$ aryloxy, substituted or unsubstituted $C_6$-$C_{20}$ heteroaryloxy, substituted or unsubstituted $C_2$-$C_{20}$ alkoxycarbonyl, substituted or unsubstituted $C_1$-$C_{20}$ acyloxy, substituted or unsubstituted $C_2$-$C_{20}$ acylamino, substituted or unsubstituted $C_{2\text{-}C20}$ alkoxycarbonylamino, substituted or unsubstituted $C_2$-$C_{20}$ aryloxycarbonylamino, substituted or unsubstituted sulfonylamino, —N(R')(R''), where R' and R'' are independently hydrogen, or a $C_1$-$C_{20}$ alkyl group, sulfamoyl, substituted or unsubstituted $C_1$-$C_{20}$ alkylcarbamoyl, carbamoyl, substituted or unsubstituted $C_6$-$C_{20}$ arylcarbamoyl, substituted or unsubstituted $C_6$-$C_{20}$ arylthio, substituted or unsubstituted $C_2$-$C_{20}$ heteroarylthio, sulfonyl, sulfinyl, ureido, phosphonic acid, amido, hydroxy, mercapto, halogen atom, cyano, carboxyl, substituted or unsubstituted $C_2$-$C_{20}$ alkylcarboxyl, nitro, hydroxamic acid, sulfino, hydrazine, imino, substituted or unsubstituted $C_1$-$C_{20}$ silylalkyl, or substituted or unsubstituted $C_1$-$C_{20}$ alkylphosphino group;

$Y_1$ and $Y_2$ are independently a halogen atom, SCN, CNO, CN, RCOO(R=substituted or unsubstituted $C_1$-$C_{20}$ alkyl, substituted or unsubstituted $C_6$-$C_{20}$ aryl, or substituted or unsubstituted $C_2$-$C_{20}$ heteroaryl), pyrazolate, imidazolate, amido, imido groups;

A is a phosphorus (P) or nitrogen (N);

Z is a substituted or unsubstituted $C_1$-$C_{20}$ alkylene, substituted or unsubstituted $C_2$-$C_{20}$ alkenylene, substituted or unsubstituted $C_6$-$C_{20}$ arylene, —O—, —S—, —P(X)—, —C(=O)—, or —Si(R)$_2$—, where X and R are independently hydrogen, a substituted or unsubstituted $C_1$-$C_{20}$ alkyl, substituted or unsubstituted $C_6$-$C_{20}$ aryl, or a halogen atom; and n is 1 or 2.

13. The organic electroluminescence device of claim 12, wherein the organic layer further comprises at least one selected from the group consisting of a mixture of a high molecular host and a low molecular host, a low molecular host, and a non-luminous high molecular matrix.

* * * * *